(12) United States Patent
Smith et al.

(10) Patent No.: US 8,485,971 B2
(45) Date of Patent: *Jul. 16, 2013

(54) SURGICAL HAND ACCESS APPARATUS

(75) Inventors: Robert C. Smith, Cheshire, CT (US); Thomas Wenchell, Durham, CT (US)

(73) Assignee: Covidien LP, Mansfield, MA (US)

( * ) Notice: Subject to any disclaimer, the term of this patent is extended or adjusted under 35 U.S.C. 154(b) by 685 days.

This patent is subject to a terminal disclaimer.

(21) Appl. No.: 12/706,780

(22) Filed: Feb. 17, 2010

(65) Prior Publication Data

US 2010/0145152 A1  Jun. 10, 2010

Related U.S. Application Data

(63) Continuation of application No. 11/102,446, filed on Apr. 5, 2005, now Pat. No. 7,717,847.

(60) Provisional application No. 60/559,548, filed on Apr. 5, 2004.

(51) Int. Cl.
  *A61B 1/32* (2006.01)

(52) U.S. Cl.
  USPC ............................................. 600/208

(58) Field of Classification Search
  USPC .................. 600/206–208, 235, 245; 128/850, 128/852, 856, 887, 897
  See application file for complete search history.

(56) References Cited

U.S. PATENT DOCUMENTS

| | | | |
|---|---|---|---|
| 2,305,289 A | 12/1942 | Coburg | |
| 3,332,417 A | 7/1967 | Blanford et al. | |
| 3,427,226 A | 2/1969 | McNeely | |
| 3,427,227 A | 2/1969 | Chamberlin | |
| 4,069,913 A | 1/1978 | Harrigan | |
| 4,984,564 A | 1/1991 | Yuen | |
| 5,159,921 A | 11/1992 | Hoover | |
| 5,342,385 A | 8/1994 | Norelli et al. | |
| 5,366,478 A | 11/1994 | Brinkerhoff et al. | |
| 5,368,545 A | 11/1994 | Schaller et al. | |
| 5,411,483 A | 5/1995 | Loomas et al. | |

(Continued)

FOREIGN PATENT DOCUMENTS

| | | |
|---|---|---|
| DE | 3737121 C2 | 5/1989 |
| DE | 4312147 A1 | 10/1993 |

(Continued)

OTHER PUBLICATIONS

European Search Report (7 pages) for corresponding EP05732709—mailing date Jul. 9, 2012.

(Continued)

*Primary Examiner* — Cris L Rodriguez
*Assistant Examiner* — Hao D Mai

(57) ABSTRACT

A surgical access apparatus adaptable to permit the sealed insertion of either the surgeon's hand and/or surgical instruments during laparoscopic and endoscopic surgical procedures includes an access housing defining a longitudinal axis and having a first internal passageway configured and dimensioned to permit passage of at least one of a hand and an arm of a surgeon, and a base mountable to the access housing. The base may include a liner member positionable within an incision of a patient to at least partially line the incision. A displacement member may be operatively connected to the access housing and to the liner member. The displacement member is adapted for movement to cause corresponding displacement of the liner member relative to the access housing whereby the liner member engages tissue forming the incision to at least partially retract the incision.

17 Claims, 3 Drawing Sheets

U.S. PATENT DOCUMENTS

| | | | |
|---|---|---|---|
| 5,480,410 A | 1/1996 | Cuschieri et al. |
| 5,514,133 A | 5/1996 | Golub et al. |
| 5,520,610 A | 5/1996 | Giglio et al. |
| 5,522,791 A | 6/1996 | Leyva |
| 5,524,644 A | 6/1996 | Crook |
| 5,526,536 A | 6/1996 | Cartmill |
| 5,545,179 A | 8/1996 | Williamson, IV |
| 5,634,911 A | 6/1997 | Hermann et al. |
| 5,636,645 A | 6/1997 | Ou |
| 5,639,937 A | 6/1997 | Hover et al. |
| 5,640,977 A | 6/1997 | Leahy et al. |
| 5,649,550 A | 7/1997 | Crook |
| 5,653,705 A | 8/1997 | de la Torre et al. |
| 5,672,168 A | 9/1997 | de la Torre et al. |
| 5,741,298 A | 4/1998 | MacLeod |
| 5,803,921 A | 9/1998 | Bonadio |
| 5,810,721 A | 9/1998 | Mueller et al. |
| 5,813,409 A | 9/1998 | Leahy et al. |
| 5,820,600 A | 10/1998 | Carlson et al. |
| 5,832,925 A | 11/1998 | Rothrum |
| 5,853,395 A | 12/1998 | Crook et al. |
| 5,899,208 A | 5/1999 | Bonadio |
| 5,906,577 A | 5/1999 | Beane et al. |
| 5,947,922 A | 9/1999 | MacLeod |
| 5,957,913 A | 9/1999 | de la Torre et al. |
| 5,964,781 A | 10/1999 | Mollenauer et al. |
| 5,997,515 A | 12/1999 | de la Torre et al. |
| 6,024,736 A | 2/2000 | de la Torre et al. |
| 6,033,426 A | 3/2000 | Kaji |
| 6,033,428 A | 3/2000 | Sardella |
| 6,042,573 A | 3/2000 | Lucey |
| 6,048,309 A | 4/2000 | Flom et al. |
| RE36,702 E | 5/2000 | Green et al. |
| 6,077,288 A | 6/2000 | Shimomura et al. |
| 6,086,570 A | 7/2000 | Aboul-Hosn et al. |
| 6,110,154 A | 8/2000 | Shimomura et al. |
| 6,123,689 A | 9/2000 | To et al. |
| 6,142,935 A | 11/2000 | Flom et al. |
| 6,142,936 A | 11/2000 | Beane et al. |
| 6,149,642 A | 11/2000 | Gerhart et al. |
| 6,159,200 A | 12/2000 | Verdura et al. |
| 6,162,172 A | 12/2000 | Cosgrove et al. |
| 6,238,373 B1 | 5/2001 | de a Torre et al. |
| 6,254,533 B1 | 7/2001 | Fadem et al. |
| 6,254,534 B1 | 7/2001 | Butler et al. |
| 6,315,770 B1 | 11/2001 | de la Torre et al. |
| 6,319,246 B1 | 11/2001 | de la Torre et al. |
| 6,382,211 B1 | 5/2002 | Crook |
| 6,440,063 B1 | 8/2002 | Beane et al. |
| 6,450,983 B1 | 9/2002 | Rambo |
| 6,482,181 B1 | 11/2002 | Racenet et al. |
| 6,578,577 B2 | 6/2003 | Bonadio et al. |
| 6,610,031 B1 | 8/2003 | Chin |
| 6,702,787 B2 | 3/2004 | Racenet et al. |
| 6,814,700 B1 | 11/2004 | Mueller et al. |
| 6,840,951 B2 | 1/2005 | de la Torre et al. |
| 6,846,287 B2 | 1/2005 | Bonadio et al. |
| 6,908,430 B2 | 6/2005 | Caldwell et al. |
| 6,942,671 B1 | 9/2005 | Smith |
| 7,052,454 B2 | 5/2006 | Taylor |
| 7,393,322 B2 | 7/2008 | Wenchell |
| 2001/0047188 A1 | 11/2001 | Bonadio et al. |
| 2002/0002324 A1 | 1/2002 | McManus |
| 2002/0019609 A1 | 2/2002 | McFarlane |
| 2002/0038077 A1 | 3/2002 | de la Torre et al. |
| 2002/0072762 A1 | 6/2002 | Bonadio et al. |
| 2003/0078478 A1 | 4/2003 | Bonadio et al. |
| 2004/0015185 A1 | 1/2004 | Ewers et al. |
| 2004/0049099 A1 | 3/2004 | Ewers et al. |
| 2004/0092795 A1 | 5/2004 | Bonadio et al. |
| 2004/0127772 A1 | 7/2004 | Ewers et al. |
| 2004/0249248 A1 | 12/2004 | Bonadio et al. |
| 2005/0020884 A1 | 1/2005 | Hart et al. |
| 2005/0148823 A1 | 7/2005 | Vaugh et al. |

FOREIGN PATENT DOCUMENTS

| | | |
|---|---|---|
| DE | 29717940 U1 | 11/1997 |
| EP | 0550069 A1 | 7/1993 |
| EP | 0 950 376 A1 | 10/1999 |
| EP | 1707133 A1 | 10/2006 |
| FR | 2710270 | 3/1995 |
| GB | 2 071 502 A | 9/1981 |
| GB | 2 255 019 A | 10/1992 |
| JP | 10-108868 | 4/1998 |
| JP | 2002028163 | 1/2002 |
| WO | WO94/04067 A1 | 3/1994 |
| WO | WO 95/04202 | 2/1995 |
| WO | WO 95/07056 | 3/1995 |
| WO | WO 95/22289 | 8/1995 |
| WO | WO 98/35614 | 8/1995 |
| WO | WO 95/27445 | 10/1995 |
| WO | WO 95/27468 | 10/1995 |
| WO | WO 96/05881 | 2/1996 |
| WO | WO 98/48724 | 11/1998 |
| WO | WO 99/25268 | 5/1999 |
| WO | WO 00/32120 | 6/2000 |
| WO | WO 00/35356 | 6/2000 |
| WO | WO 00/54675 | 9/2000 |
| WO | WO 00/54676 | 9/2000 |
| WO | WO 00/54677 | 9/2000 |
| WO | WO 01/08563 A2 | 2/2001 |
| WO | WO 01/08581 A2 | 2/2001 |
| WO | WO02/17800 A2 | 3/2002 |
| WO | WO03/007821 A1 | 1/2003 |
| WO | WO03/043683 A1 | 5/2003 |
| WO | WO2006/110733 A2 | 10/2006 |
| WO | WO2008/121294 A1 | 10/2008 |
| WO | WO2008149332 A1 | 12/2008 |

OTHER PUBLICATIONS

European Search Report for corresponding EP09250324 dated Jul. 25, 2011.

SURGICAL HAND ACCESS APPARATUS

CROSS-REFERENCE TO RELATED APPLICATION(S)

This application is a continuation of co-pending U.S. patent application Ser. No. 11/102,446, filed Apr. 5, 2005, now U.S. Pat. No. 7,717,847, issued on May 18, 2010, which claims benefit to U.S. Provisional Application No. 60/559,548, filed Apr. 5, 2004. The entire contents of both applications are hereby incorporated herein by reference.

BACKGROUND

1. Field of the Disclosure

The present disclosure relates generally to surgical devices for facilitating sealed access across a body wall and into a body cavity and, more particularly, to a surgical access apparatus adaptable to permit the sealed insertion of either the surgeon's hand and/or surgical instruments during laparoscopic and endoscopic surgical procedures.

2. Description of the Related Art

Minimally invasive surgical procedures including both endoscopic and laparoscopic procedures permit surgery to be performed on organs, tissues and vessels far removed from an opening within the tissue. Laparoscopic and endoscopic procedures generally require that any instrumentation inserted into the body be sealed, i.e. provisions must be made to ensure that gases do not enter or exit the body through the incision as, e.g., in surgical procedures in which the surgical region is insufflated. These procedures typically employ surgical instruments which are introduced into the body through a cannula. The cannula has a seal assembly associated therewith. The seal assembly provides a substantially fluid tight seal about the instrument to preserve the integrity of the established pneumoperitoneum.

Minimally invasive procedures have several advantages over traditional open surgery, including less patient trauma, reduced recovery time, reduced potential for infection, etc. However, despite the recent success and overall acceptance of minimally invasive procedures as a preferred surgical technique, minimally invasive surgery, such as laparoscopy, has several disadvantages. In particular, surgery of this type requires a great deal of surgeon skill in order for the surgeon to manipulate the long narrow endoscopic instruments about a remote site under endoscopic visualization. In addition, in laparoscopic surgery involving the intestinal tract, it is often preferable to manipulate large sections of the intestines to perform the desired procedure. These manipulations are not practical with current laparoscopic tools and procedures accessing the abdominal cavity through a trocar or cannula.

To address these concerns, recent efforts have focused on hand-assisted laparoscopic techniques and procedures. These procedures incorporate both laparoscopic and conventional surgical methodologies. The hand assisted technique is performed in conjunction with a hand access seal which is an enlarged device positionable within the incision in, e.g., the insufflated abdominal cavity. The device includes a seal for forming a seal about the surgeon's arm upon insertion while permitting surgical manipulation of the arm within the cavity. However, known hand access seals are quite cumbersome and incorporate elaborate sealing mechanisms. Moreover, these hand access seals are incapable of conversion for use with laparoscopic instruments.

SUMMARY

Accordingly, the present disclosure relates to a surgical access apparatus adaptable to permit the sealed insertion of either the surgeon's hand and/or surgical instruments during laparoscopic and endoscopic surgical procedures. The surgical access apparatus includes an access housing defining a longitudinal axis and having a first internal passageway configured and dimensioned to permit passage of at least one of a hand and an arm of a surgeon, and a base mountable to the access housing. The base may include a liner member positionable within an incision of a patient to at least partially line the incision. The liner member may have a first end for positioning within the body and a second end for positioning external of the body. A displacement member may be operatively connected to the access housing and to the second end of the liner member. The displacement member is adapted for movement to cause corresponding displacement of the second end of the liner member relative to the access housing whereby the liner member engages tissue forming the incision to at least partially retract the incision.

The surgical access apparatus may include a seal mounted to the access housing across the first internal passageway. The seal may be adapted to receive the hand and/or the arm of the surgeon in a substantial fluid-tight relation. One seal comprises a gel material.

The surgical access apparatus further may include a trocar adapter releasably mountable to the access housing in the absence of the at least one of the hand and the arm. The trocar adapter includes a trocar sleeve having a second internal passageway dimensioned to permit passage of a surgical instrument. The trocar adapter may include an instrument valve disposed relative to the second internal passageway. The instrument valve may be adapted to establish a substantial fluid tight relation with the instrument. The seal of the access housing may be adapted to form a substantial fluid tight seal about the trocar sleeve of the trocar adapter.

The displacement member may include an expandable member. The access housing may include an outer trough for at least partial reception of the expandable member.

The base may include a housing mount mounted to the access housing and positioned adjacent the expandable member. The housing mount is operatively coupled to the second end of the liner member and is movable relative to the access housing upon expansion of the expandable member to displace the second end of the liner member. The base also may include first and second substantially annular members connected adjacent respective first and second ends of the liner member. The second substantially annular member may be operatively coupled to the housing mount. The first annular member may comprise a resilient material.

In another embodiment, a surgical access apparatus includes an access housing having a housing passageway for receiving an object, a seal mounted to the access housing across the housing passageway, and a base mountable to the access housing. The seal is adapted to receive the at least one of the hand and the arm in substantial fluid-tight relation. The base includes a flexible liner member which is positionable within an incision of a patient to at least partially line the incision and has a first end for positioning within the body to engage an inner surface of the body and a second end for positioning external of the body; a substantially annular housing mount mounted with respect to the access housing and operatively coupled to the second end of the liner member and a substantially annular expandable member in operative engagement with the housing mount. The expandable member is expandable to displace the housing mount and the second end of the liner member whereby the liner member engages tissue forming the incision to at least partially retract the incision. The base may include first and second substantially annular members connected adjacent respective first and second ends of the liner member. The housing mount may be in operative engagement with the second member. The access housing may include an outer trough with the expandable member being at least partially accommodated in the outer trough.

A trocar adapter may be releasably mountable to the access housing in the absence of the at least one of the hand and the arm. The trocar adapter includes a trocar sleeve having a sleeve passageway dimensioned to permit passage of a surgical instrument and an instrument valve adapted to establish a substantial fluid tight relation with the instrument.

In a still further embodiment, the surgical access apparatus may include an access housing defining a central longitudinal axis and having a longitudinal opening extending therethrough for passage of a surgeon's hand. A retractor base may be mounted to the access housing. The retractor base may include a flexible liner for positioning within the incision to engage tissue portions defining the incision. A trocar adapter may be releasably mounted to the access housing. The trocar adapter may include a trocar sleeve positioned for reception within the longitudinal opening of the access housing when the trocar adapter is mounted to the access housing, the trocar sleeve having an internal passageway for passage of a surgical instrument. An instrument valve having inner valve portions dimensioned and configured to receive a surgical instrument in fluid tight relation therewith. A zero closure valve adapted to open to permit passage of the surgical instrument and substantially close in the absence of the surgical instrument. A seal mounted to the access housing, the seal having internal seal portions dimensioned and configured to establish a sealing relation with the surgeon's arm or with the trocar sleeve when the trocar adapter is mounted to the access housing in the absence of the surgeon's arm.

In another embodiment, a surgical access apparatus includes an access housing defining a central longitudinal axis and having a longitudinal opening extending therethrough for passage of a surgeon's hand, a retractor base mounted to the access housing and having a flexible liner for positioning within the incision to engage tissue portions defining the incision, a trocar adapter releasably mounted to the access housing, and a seal mounted to the access housing. The trocar adapter includes a trocar sleeve positioned for reception within the longitudinal opening of the access housing when the trocar adapter is mounted to the access housing and having an internal passageway for passage of a surgical instrument, an instrument valve having inner valve portions dimensioned and configured to receive a surgical instrument in fluid tight relation therewith and a zero closure valve adapted to open to permit passage of the surgical instrument and substantially close in the absence of the surgical instrument. The seal mounted to the access housing has internal seal portions dimensioned and configured to establish a sealing relation with the surgeon's arm or with the trocar sleeve when the trocar adapter is mounted to the access housing in the absence of the surgeon's arm.

Methods for performing hand assisted and instrument assisted laparoscopic surgical procedures are also envisioned.

These and other embodiments of the present disclosure will be described herein below in greater detail.

BRIEF DESCRIPTION OF THE DRAWINGS

Preferred embodiments of the present disclosure will be better appreciated by reference to the drawings wherein.

DETAILED DESCRIPTION OF THE PREFERRED EMBODIMENTS

The surgical access apparatus of the present disclosure provides a substantial seal between the body cavity of a patient and the outside atmosphere before, during and after insertion of an object through the apparatus. The apparatus has a flexible liner and an expandable member so that the apparatus can be used to line the incision and to retract the incision, providing access to a surgical site.

Moreover, the access apparatus of the present invention is capable of accommodating the hand and/or arm of a surgeon and is convertible to receive surgical instruments of varying diameters, which may range from 5 mm to 15 mm, for example, and establishing a gas tight seal with the arm and each instrument when inserted. The access apparatus is further adapted to substantially seal the body cavity in the absence of the object to maintain the integrity of the insufflated peritoneal cavity.

Generally, the access apparatus is convertible between a first operative condition to permit introduction and manipulation of a surgeon's hand or arm in sealed relation therewith and a second operative condition to permit introduction and manipulation of a laparoscopic or endoscopic surgical instrument also in sealed relation.

Although the specific focus of this disclosure will be on a preferred laparoscopic procedure, it will be noted that laparoscopic surgery is merely representative of a type of operation wherein a procedure can be performed in a body cavity through an access apparatus through a body wall.

In the following description, as is traditional the term "proximal" refers to the portion of the instrument closest to the operator, while the term "distal" refers to the portion of the instrument remote from the operator.

Figure 1:
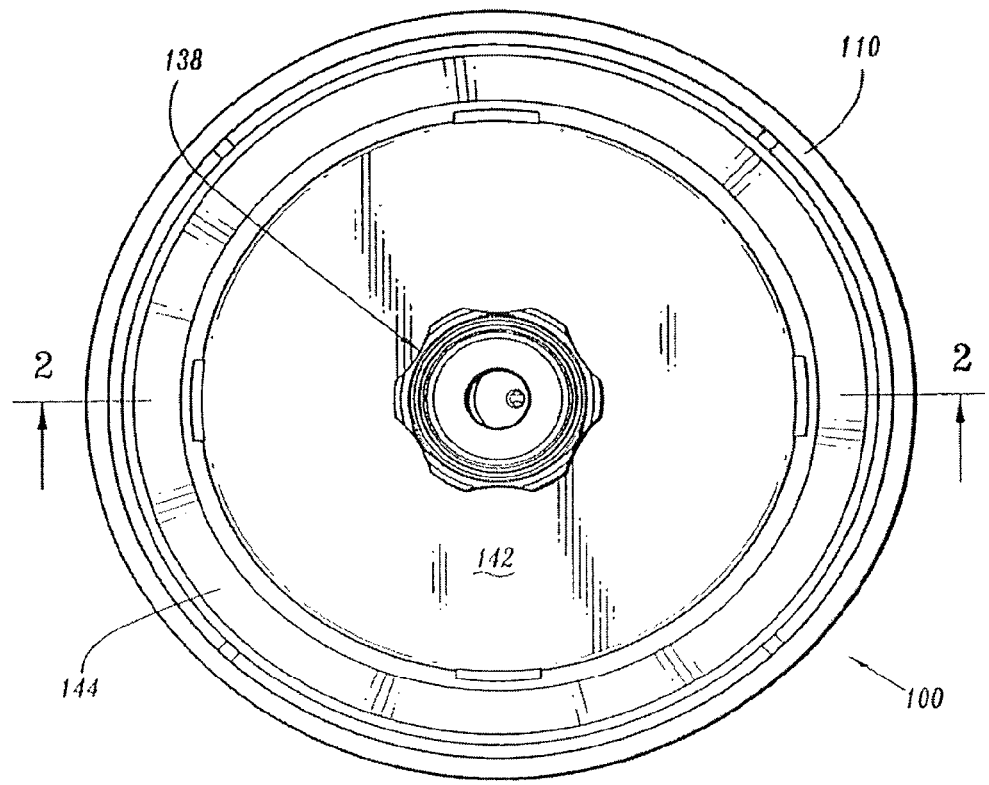
FIG. 1 is a top view of the hand access apparatus in accordance with the principles of the present disclosure illustrating the access housing, trocar adapter and retractor base.
Figure 2:
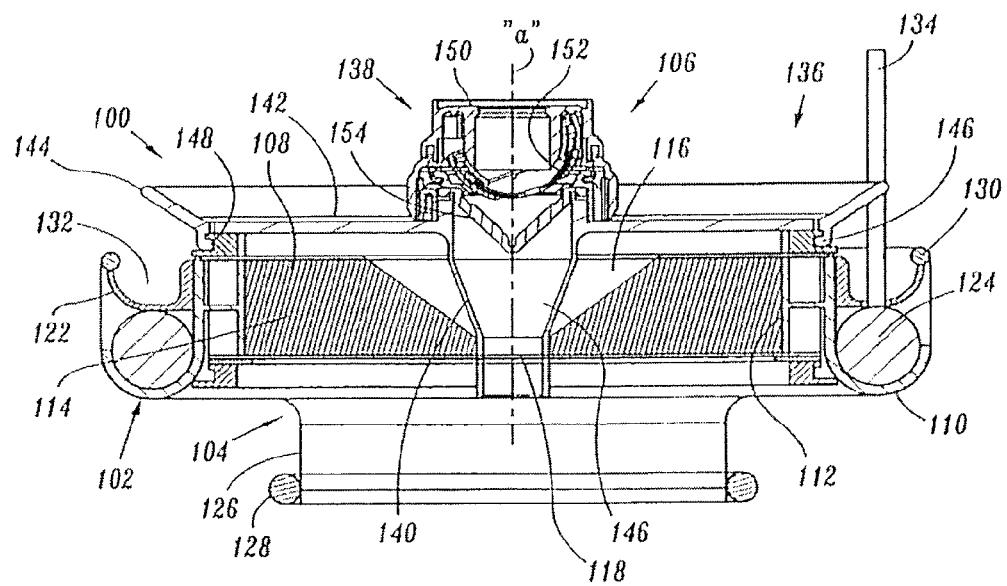
FIG. 2 is a cross sectional view of the access apparatus in accordance with the embodiment of FIG. 1 taken along lines 2-2 of FIG. 1.

Referring now to the drawings, in which like reference numerals identify identical or substantially similar parts throughout the several views, FIGS. 1 and 2 illustrate the access apparatus of the present disclosure. Access apparatus 100 includes two main components, namely, access housing 102 and retractor base 104. The apparatus also desirably includes trocar adapter 106, which is releasably mounted to the access housing 102. Access housing 102 is intended for positioning adjacent (preferably, in contact with) the external area of the body, e.g., the abdominal cavity. Access housing 102 defines central longitudinal axis "a" and longitudinal opening or passageway 108 extending along the central axis "a". Longitudinal passageway 108 is dimensioned to permit passage of the surgeon's hand and/or arm. Access housing 102 further includes an outer circumferential U-shaped flange or trough 110 and an internal vertical support wall 112. Although vertical support wall 112 is shown as having an inner and outer wall, a single wall may be used. Vertical support wall 112 defines longitudinal passageway 108. Access housing 102 may be made from any suitable biocompatible polymeric material including polycarbonate, polystyrene, etc. Alternatively, access housing 102 may be fabricated from biocompatible metals such as stainless steel or titanium and their alloys.

Referring still to FIGS. 1-2, access housing 102 preferably includes a seal 114 which is mounted across longitudinal passageway 108. Seal 114 may comprise one or more seals, such as septum seals, flapper valves, duckbill seals, etc., arranged to provide a substantial seal around a surgeon's arm, or surgical instruments, or in the presence of such object. The embodiment of FIGS. 1-7 has a gel material such as a soft urethane gel, silicon gel, etc. and preferably has compressible characteristics to permit the seal 114 to conform and form a seal 114 about the outer surface of a surgeon's hand and/or arm during insertion and manipulation about the operation site. Seal 114 preferably includes a V-shaped entrance opening 116 which extends to slit 118 within the seal 114. V-shaped opening 116 converges inwardly toward slit 118 to facilitate insertion and passage of an object such as a surgeon's hand and/or adapter 106 through seal 114. Moreover, seal 114 opens to permit passage of the object whereby the internal gel portions defining slit 118 engage this object in fluid tight relation therewith. Seal 114 is further adapted to assume a substantially closed position in the absence of the hand or adapter 106, i.e., to form a zero seal, thus preventing the escape of insufflation gases through access housing 102 when objects have been removed from the passageway 108 of access apparatus 100. Slit 118 of seal 114 may be a generally linear orientation, t-shaped, tricuspid, or x-shaped, or other shape when viewed in plan. Seal 114 is connected to the interior of access housing 102 through conventional means such as being molded therewith or connected therewith by an adhesive.

In an alternate preferred embodiment, seal 118 is fabricated from a resilient material, e.g., polyisoprene, and has at least one layer of fabric material positioned adjacent the resilient material, or molded with the resilient material. A friction resisting coating may be applied to seal 118. Seals such as those disclosed in certain embodiments of commonly-assigned U.S. patent application Ser. No. 10/165,373 filed Jun. 6, 2002, the contents of which are incorporated in its entirety by reference, may be used. Other valve types are also contemplated including zero-closure valves, septum valves, slit valves, double-slit valves, inflatable bladders, other foam or gel valve arrangements, etc.

Figure 3:
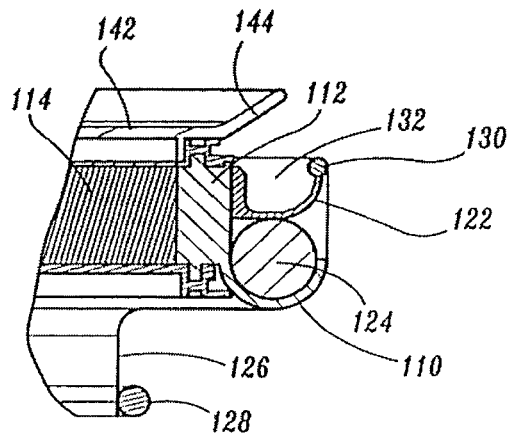
FIG. 3 is a partial cross-sectional view of the access apparatus in accordance with the embodiment of FIG. 1 taken along lines 3-3 of FIG. 1.
Figure 4:
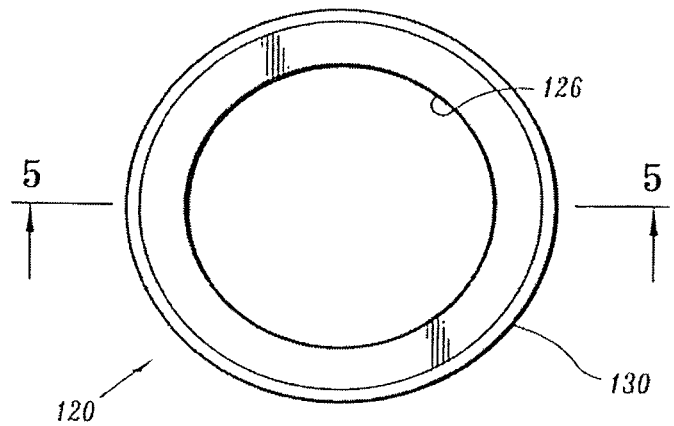
FIG. 4 is a top plan view of the expandable member of the retractor base of the access apparatus in accordance with the embodiment of FIG. 1.
Figure 5:
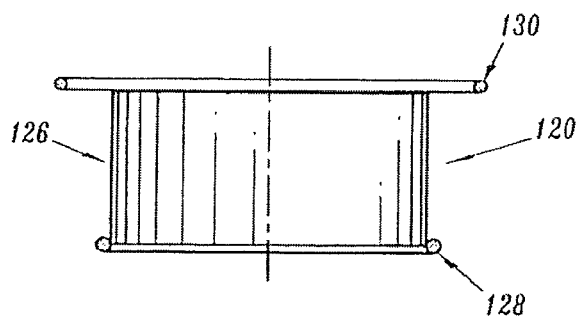
FIG. 5 is a side cross-sectional view of the expandable member in accordance with the embodiment of FIG. 1 taken along lines 5-5 of FIG. 4.

Referring now to FIGS. 1-3, retractor base 104 will be discussed. Retractor base 104 is intended for positioning within the incision of the patient to line the incision and/or retract the tissue defining the incision thereby enhancing access to the underlying body cavity. Retractor base 104 includes liner 120, annular mount 122 at the wall end of retractor base 104 and expandable member 124 disposed in the u-shaped through 110 of access housing 102. With reference to FIGS. 4-5, in conjunction with FIGS. 1-3, liner 120 includes tubular sheath or flexible liner member 126, first member 128 connected to other end of the liner member 126 and second member 130 connected to the remaining end of the liner member 126. Liner member 126 may be a sheet of flexible material including, for example, polyethylene, polypropylene, etc., arranged in a tubular configuration. Liner member 126 may also include an elastomeric material and may incorporate rigid runners embedded within the material to increase its rigidity. Although in the preferred embodiment, liner member 126 is tubular, it is envisioned that the liner member 126 may incorporate several pieces, e.g., individual tabs or the like. Liner member 126 may or may not be impervious to fluids. Liner member 126 is desirably adapted to line the incision so as to prevent contamination of the incision by any tissue which may be removed through the access apparatus, or in the course of the surgery. Generally, liner member 126 serves to retract the incision during placement of the retractor base 104, so that the patient's skin, fascia, and other tissue are drawn back, allowing access to the surgical site.

First member 128 of liner 120 is adapted for positioning through the incision and beneath the abdominal wall to engage the interior abdominal wall portions to thereby secure retractor base 104 relative to the incision. First member 128 is preferably flexible to facilitate passage through the incision and possesses sufficient resiliency to return to its original configuration upon entering the abdominal cavity. First member 128 is preferably annular or ring-like in configuration and may be fabricated from a resilient or elastomeric material. First member 128 may be fixedly secured to the end of liner member 126 through conventional means such as welding, adhesives, etc. . . . .

Second member 130 is also annular or ring-like in configuration and is attached to the other end of liner member 126 by conventional means such as welding, adhesives, etc. . . . . Second member 130 preferably possesses a more rigid characteristic than first member 128, and may be formed of a suitable biocompatible polymeric material or a biocompatible metal. Alternatively, second member 130 may be fabricated from an elastomeric material. Alternatively, the first member 128 and second member 130 may be formed integrally with the liner member 126. The second member 130 may be omitted.

As best depicted in FIGS. 2-3, annular mount 122 of retractor base 104 is coaxially mounted about access housing 102. Annular mount 122 is adapted to move relative to access housing 102 in a longitudinal direction relative to longitudinal axis "a" and preferably slides along the outer surface of the vertical support wall of the access housing 102 adjacent vertical support wall 112. Annular mount 122 is adapted to connect to second member 130 in a manner which secures the second member 130 to the annular mount 122. Any suitable means to connect second member 130 to annular mount 122 are envisioned including adhesives, cements etc. Alternatively, a snap-fit or ridge for receiving the second member 130 may be used. Annular mount 122 and second member 130 may incorporate corresponding structure to securely mount the two components. Such structure may be a tongue and groove arrangement, tab and slot etc. . . . . In one preferred embodiment, second member 130 is pulled over to be received within inner channel 132 of annular mount 122 and may be retained within the channel 132 through a friction fit, the resiliency of the second member, or the like. Alternatively, the upper end of the liner member 126 may be wrapped around annular mount 122.

Figure 6:
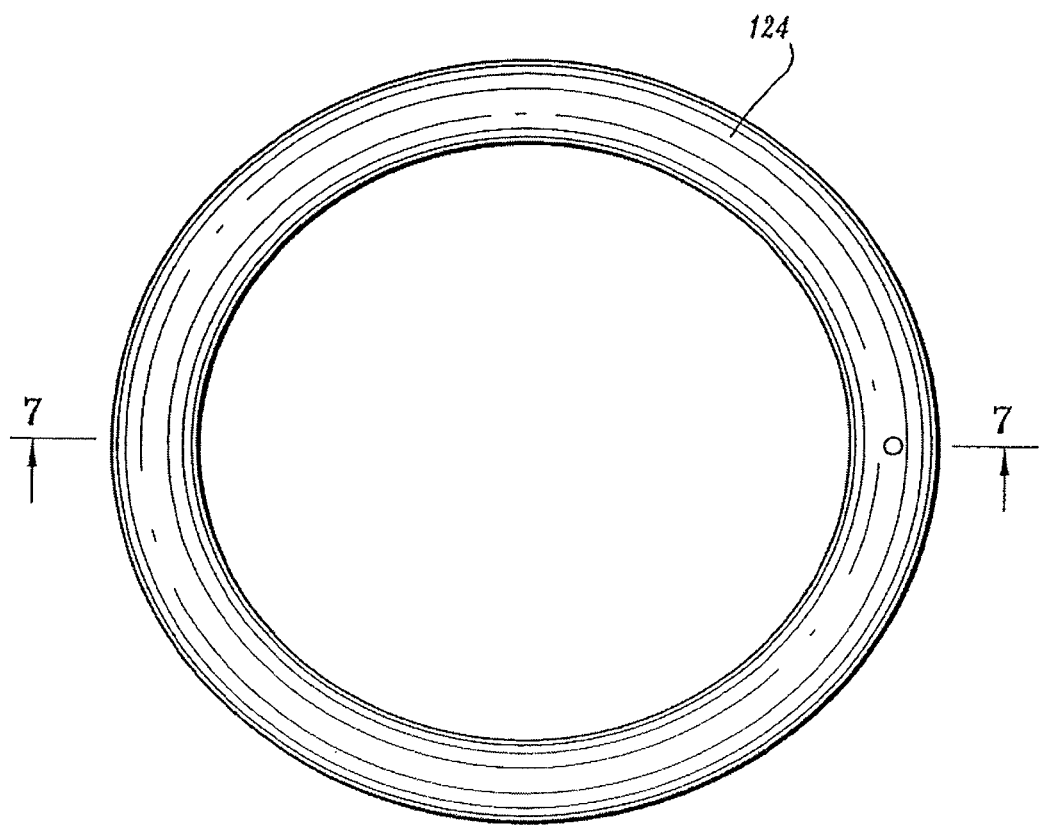
FIG. 6 is a top plan view of the flexible liner of the retractor base of the access apparatus in accordance with the embodiment of FIG. 1.
Figure 7:
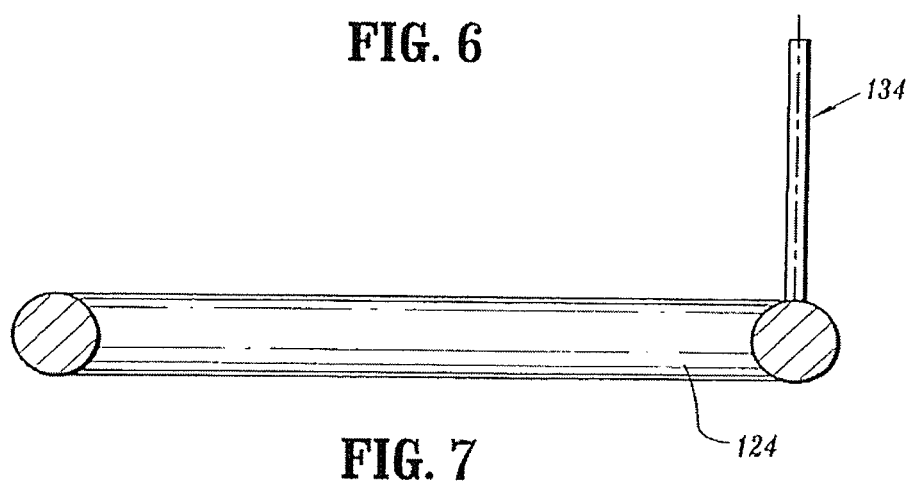
FIG. 7 is a side cross-sectional view of the flexible liner in accordance with the embodiment of FIG. 1 taken along lines 7-7 of FIG. 6.

With reference now to FIGS. 6-7, in conjunction with FIGS. 1-3, expandable member 124 of retractor base 104 is preferably in the form of a balloon having an annular or ring like dimension correspondingly arranged to be received and confined within outer trough 110 of access housing 102. Expandable member 124 includes a fluid supply line 134 which is in communication with the interior of the expandable member 124 to provide fluid to, and selectively inflate, the expandable member 124. Expandable member 124 may be selectively filled with a fluid such as water, saline, etc. or a gas such as air or $CO_2$. In the assembled condition of apparatus 100, the upper surface of expandable member 124 contacts annular mount 122. Accordingly, upon expansion of expandable member 124, annular mount 122 is displaced in a proximal direction away from the abdominal cavity. Similarly, second member 130 attached to annular mount 122 also moves proximally away from first member 128. Such movement causes liner member 126 to become tensioned, thereby drawing the tissue surrounding the incision laterally outwardly to at least partially retract the incision. Liner member 126 is tensioned so as to retract the incision, without requiring the surgeon to pull on the liner member 126, or arrange the liner member 126 and fix the liner member 126 in position. As appreciated, as liner member 126 is tensioned, first member 128 may be also pulled in a proximal direction to bring the first member 128 into contact with the interior wall of the abdominal cavity. This activity effectively secures retractor base 104 within the incision and seals against the leakage of gas around the sleeve.

Referring again to FIGS. 1-2, trocar adapter 106 of access apparatus 100 will now be described. Trocar adapter 106 includes adapter base 136 and valve assembly 138 which is mounted to the adapter base 136. Adapter base 136 includes cannula sleeve 140, inner wall 142 extending from the sleeve 140 and peripheral flange 144. Cannula sleeve 140 is a tubelike structure having a longitudinal opening 146 dimensioned for passage of surgical instrumentation. The proximal end of cannula sleeve 140 extends beyond inner wall 142 for attachment to valve assembly 138 as will be discussed. Adapter base 136 is preferably monolithically formed as a single unit and may be fabricated from a suitable biocompatible polymeric material through injection molding techniques, or using other known techniques. Alternatively, adapter base 136 may be formed of a suitable biocompatible metal material like stainless steel, titanium, titanium alloys etc.

Adapter base 106 is preferably releasably mounted to access housing 102. In one preferred arrangement, adapter base 106 includes peripheral rib 146 extending radially inwardly relative to longitudinal axis "a". Peripheral rib 146 is received within annular groove 148 of access housing 102 in snap-fit relation therewith to releasably connect the two components. Other means for releasably connecting adapter base 106 to access housing 102 are also envisioned including a bayonet coupling, friction fit, tongue and groove, etc. Adapter base 106 may also be tethered to access housing 102 to provide a flip-top arrangement.

Valve assembly 138 may be any conventional trocar seal system adapted for mounting to a cannula sleeve and forming a fluid tight seal about an endoscopic instrument ranging in diameter from about 3 mm to about 15 mm. In one preferred embodiment, valve assembly 138 is of the type available from United States Surgical Corporation of Norwalk, Conn. under the tradename, VERSAPORT™ PLUS. The VERSAPORT™ PLUS seal includes a valve housing 150, a semicircular or hemispherical gimbal valve 152 mounted within the housing and a zero-closure or duck-bill valve 154 extending from the valve housing 150 and toward cannula sleeve 140. Gimbal valve 152 is adapted to swivel or rotate within valve housing 150 about a central axis of rotation to accommodate offset manipulation of the instrument inserted through valve assembly 138. Gimbal valve 152 includes a mounting that is rotatably secured in the valve housing 150 and a resilient valve member for forming a seal with the instrument. Duck bill valve 154 is adapted to open in the presence of an instrument and close to function as a zero closure seal in the absence of an instrument. Valve housing 150 is connected to the proximal end of cannula sleeve 140 through any conventional means including adhesives, bayonet coupling, etc. Other valve assemblies for incorporation into adapter 106 are also envisioned such as the valve assemblies disclosed in commonly assigned U.S. Pat. Nos. 6,482,181, 5,820,600, U.S. Pat. Reissue No. 36,702 and U.S. patent application Ser. No. 09/706,643, filed Nov. 6, 2000, the entire contents of each are hereby incorporated by reference herein.

Other details of trocar adapter 106 may be ascertained by reference to the commonly assigned U.S. Pat. No. 7,393,322, which is incorporated herein in its entirety by reference.

Operation

The use of the access apparatus 100 in connection with a hand assisted laparoscopic surgical procedure will be discussed. Generally, the peritoneal cavity is insufflated using e.g., a trocar, and an incision is made to provide access to the cavity as is conventional in the art. Thereafter, retractor base 104 is introduced within the incision by contracting first member 128 and advancing the first member 128 through the incision and into the body cavity. First member 128 is released to permit the first member 128 to return to its normal condition (under the influences of its inherent resiliency) within the cavity. Liner member 126 extends from first member 128 through the incision to line the incision as previously discussed.

The procedure is continued by positioning access housing 102 (without adapter 106 being attached to access housing 102) adjacent the external side of the abdominal wall. If not already connected, second member 130 is connected to annular mount 122 by positioning the second member 130 within channel 132 of annular mount 122. Thereafter, expandable member 124 which is received within outer trough 110 of access housing 102 is expanded by introduction of fluids through supply line 134. During expansion, annular mount 122 (through its contact with expandable member 124) is displaced from the patient to slide proximally along the vertical support wall 112 of access housing 102 to thereby also displace second member 130 of liner 120 in a proximal direction. This movement causes any excess slack in liner member 126 to be removed and draws first member 128 into further engagement with the internal abdominal wall thereby securing retractor base 104 relative to the body tissue. As appreciated, liner member 126 may also expand the size of the incision upon movement of second member 130.

With access apparatus 100 in its first operative condition, hand assisted surgery may then be effected by advancement of the surgeon's hand and arm through seal 114 of access housing 102 and into the body cavity. Seal 114 forms a fluid tight seal about the arm. The desired hand assisted procedure may then be performed.

When it becomes desirable to convert hand access apparatus 100 for use with laparoscopic instrumentation (i.e., to convert access apparatus 100 to its second operative condition), trocar adapter 106 is mounted to access housing 102 in the aforedescribed manner. Once mounted, trocar sleeve 140 extends through slit 118 of seal 114. Seal 114 forms a fluid-tight seal about the outer surface of trocar sleeve 140. Instrumentation is introduced through valve assembly 138 and trocar sleeve 140 to carry out the desired procedures. As mentioned, gimbal valve 140 of valve assembly 138 forms a fluid tight seal about the instrument and permits manipulation of the instrument within the operative site.

Thus, access apparatus 100 may be utilized in conjunction with hand-assisted laparoscopic procedures and more conventional instrument-assisted laparoscopic procedures. This flexibility and adaptability significantly reduces the number of incisions required within the abdominal cavity thus minimizing patient trauma and infection, and improving recovery time.

It will be understood that various modifications may be made to the embodiments disclosed herein. Therefore, the above description should not be construed as limiting, but merely as exemplifications of preferred embodiments. Those skilled in the art will envision other modifications within the scope and spirit of the claims appended hereto.

What is claimed:

1. A surgical access apparatus, which comprises:
an access housing defining a longitudinal axis, and having a support wall generally extending along the longitudinal axis and forming a first internal passageway configured and dimensioned to permit passage of at least one of a hand and an arm of a surgeon; and
a base mountable to the access housing, the base including:
a housing mount coaxially mounted about the support wall of the access housing and adapted for longitudinal sliding movement along the support wall;
a liner member positionable within an incision of a patient to at least partially line the incision, the liner member having a first end for positioning within the body and a second end for positioning external of the body and being connected to the housing mount; and
a displacement member operatively connected to the access housing and to the second end of the liner member, the displacement member adapted for movement to cause longitudinal sliding movement of the housing mount along the support wall and relative to the access housing, and corresponding displacement of the second end of the liner member relative to the access housing whereby the liner member engages tissue forming the incision to at least partially retract the incision.

2. The surgical access apparatus according to claim 1 including a seal mounted to the access housing across the first internal passageway, the seal adapted to receive the at least one of the hand and the arm in substantial fluid-tight relation.

3. The surgical access apparatus according to claim 2 wherein the displacement member includes an expandable member.

4. The surgical access apparatus according to claim 3 wherein the base includes a housing mount mounted to the access housing and positioned adjacent the expandable member, the housing mount operatively coupled to the second end of the liner member and movable relative to the access housing upon expansion of the expandable member to displace the second end of the liner member.

5. The surgical access apparatus according to claim 4 wherein the base includes first and second substantially annular members connected adjacent respective first and second ends of the liner member.

6. The surgical access apparatus according to claim 5 wherein the second substantially annular member is operatively coupled to the housing mount.

7. The surgical access apparatus according to claim 5 wherein the first annular member comprises a resilient material.

8. The surgical access apparatus according to claim 2 wherein the seal is a passive seal, the passive seal having internal seal portions comprising a resilient material and being adapted move from a normally biased closed position substantially closing the first internal passageway to an activated open position receiving the at least one of the hand and the arm of the surgeon in substantial fluid-tight relation.

9. A surgical access apparatus, which comprises:
an access housing defining a longitudinal axis and having a first internal passageway configured and dimensioned to permit passage of at least one of a hand and an arm of a surgeon and a seal mounted across the first internal passageway; and
a base mountable to the access housing, the base including:
a liner member positionable within an incision of a patient to at least partially line the incision, the liner member having a first end for positioning within the body and a second end for positioning external of the body;
a displacement member operatively connected to the access housing and to the second end of the liner member, the displacement member adapted for movement to cause corresponding displacement of the second end of the liner member relative to the access housing whereby the liner member engages tissue forming the incision to at least partially retract the incision; and
a trocar adapter releasably mountable to the access housing in the absence of the at least one of the hand and the arm, the trocar adapter including a trocar sleeve having a second internal passageway dimensioned to permit passage of a surgical instrument, the trocar sleeve dimensioned to extend through the seal of the access housing when mounted to the access housing whereby the seal establishes a sealing relation with the trocar sleeve.

10. The surgical access apparatus according to claim 9 wherein the trocar adapter includes an instrument valve disposed relative to the second internal passageway, the instrument valve adapted to establish a substantial fluid tight relation with the instrument.

11. The surgical access apparatus according to claim 10 wherein the seal comprises a gel material.

12. A surgical access apparatus, which comprises:
an access housing defining a longitudinal axis, and having a first internal passageway configured and dimensioned to permit passage of at least one of a hand and an arm of a surgeon, the access housing having an outer trough; and
a base mountable to the access housing, the base including:
a liner member positionable within an incision of a patient to at least partially line the incision, the liner member having a first end for positioning within the body and a second end for positioning external of the body; and
an expandable member at least partially disposed within the outer trough and operatively connected to the access housing and to the second end of the liner member, the expandable member adapted for expansion to cause corresponding displacement of the second end of the liner member relative to the access housing whereby the liner member engages tissue forming the incision to at least partially retract the incision.

13. A surgical access apparatus which comprises:
an access housing having a housing passageway for receiving an object and defining a longitudinal axis;
a seal mounted to the access housing across the housing passageway, the seal adapted to receive the at least one of the hand and the arm in substantial fluid-tight relation; and
a base mountable to the access housing, the base including:
a flexible liner member positionable within an incision of a patient to at least partially line the incision and having a first end for positioning within the body to engage an inner surface of the body and a second end for positioning external of the body;

a substantially annular housing mount mounted with respect to the access housing and operatively coupled to the second end of the liner member, the annular housing mount coaxially arranged with respect to the longitudinal axis and slidable relative to the access housing in a general longitudinal direction; and a substantially annular expandable member in operative engagement with the housing mount, the expandable member expandable to displace the housing mount and the second end of the liner member whereby the liner member engages tissue forming the incision to at least partially retract the incision.

14. The surgical access apparatus according to claim 13 wherein the base includes first and second substantially annular members connected adjacent respective first and second ends of the liner member, the housing mount in operative engagement with the second member.

15. The surgical access apparatus according to claim 13 including a trocar adapter releasably mountable to the access housing in the absence of the at least one of the hand and the arm, the trocar adapter including a trocar sleeve having a sleeve passageway dimensioned to permit passage of a surgical instrument and an instrument valve adapted to establish a substantial fluid tight relation with the instrument.

16. The surgical access apparatus according to claim 15 wherein the trocar sleeve is dimensioned to extend through the seal of the access housing when mounted to the access housing whereby the seal establishes a sealing relation with the trocar sleeve.

17. A surgical access apparatus, which comprises:

an access housing having a housing passageway for receiving an object, the access housing having an outer trough;

a seal mounted to the access housing across the housing passageway, the seal adapted to receive the at least one of the hand and the arm in substantial fluid-tight relation; and a base mountable to the access housing, the base including:
   a flexible liner member positionable within an incision of a patient to at least partially line the incision and having a first end for positioning within the body to engage an inner surface of the body and a second end for positioning external of the body;
   a substantially annular housing mount mounted with respect to the access housing and operatively coupled to the second end of the liner member;
   a substantially annular expandable member in operative engagement with the housing mount and being at least partially accommodated in the outer trough, the expandable member expandable to displace the housing mount and the second end of the liner member whereby the liner member engages tissue forming the incision to at least partially retract the incision.

* * * * *